United States Patent [19]
Barrett et al.

[11] Patent Number: 5,185,131
[45] Date of Patent: Feb. 9, 1993

[54] LASING DYE SENSOR FOR CHEMICAL VAPORS

[75] Inventors: Terence W. Barrett, Bethesda; John F. Giuliani, Kensington, both of Md.

[73] Assignee: The United States of America as represented by the Secretary of the Navy, Washington, D.C.

[21] Appl. No.: 802,926

[22] Filed: Dec. 6, 1991

Related U.S. Application Data

[62] Division of Ser. No. 245,421, Sep. 16, 1988, Pat. No. 5,108,931.

[51] Int. Cl.$^5$ .............................................. G01N 21/27
[52] U.S. Cl. ....................................... 422/91; 422/88; 356/318; 356/440; 372/53; 372/54
[58] Field of Search ............... 356/318, 436, 437, 440; 372/51–59; 422/88, 91

[56] References Cited

U.S. PATENT DOCUMENTS

| | | | |
|---|---|---|---|
| 4,154,579 | 5/1979 | Kreisel | 23/232 E |
| 4,298,845 | 11/1981 | Laude | 331/94.5 C |
| 4,650,329 | 3/1987 | Barrett et al. | 356/345 |

Primary Examiner—James C. Housel
Assistant Examiner—David Redding
Attorney, Agent, or Firm—Thomas E. McDonnell; Barry A. Edelberg

[57] ABSTRACT

In an external lasing dye sensor system, a stream of lasing dye free-flows across an open area inside a chamber. An air sample comprising chemical vapor contaminants is pumped or drawn into the chamber. A laser beam is introduced into the chamber intersecting the lasing dye. A chemical reaction between the contaminants and the lasing dye result in a change in the emission spectra of the lasing dye. The change in emission spectra is detected and thus provides an improved apparatus for detecting low concentrations of chemical vapors in an air sample.

14 Claims, 3 Drawing Sheets

LASING DYE SENSOR FOR CHEMICAL VAPORS

This is a division of application Ser. No. 245,421 filed on Sep. 16, 1988, now U.S. Pat. No. 5,108,931.

BACKGROUND OF THE INVENTION

1. Field of the Invention

This invention relates to an analytical device for atmospheric analysis and, more specifically, to a device for detecting low concentrations of chemical vapors by use of a lasing dye sensor system.

2. Description of the Prior Art

In the past, detection of chemical vapors by means of a laser has been accomplished by monitoring or analyzing spectra of the sample gas. Previous devices and methods used a cavity which holds a sample gas or absorber media, such as a dye or a reference gas, to modify the laser beam to detect the presence of a particular chemical vapor.

Parli et al describes using intracavity absorption to detect hydrocarbons with a helium-neon laser operating at the 3.39 micron and 0.63 micron lines in the spectra ("Helium-Neon Laser Intracavity Absorption Detector for Gas Chromatography", Parli et al, Anal. Chem., Vol.54, p.1969, (1987)). Hydrocarbons absorb at 3.39 microns. The 0.63 micron line intensity is a quantitative measure of the concentration. However, only molecules which absorb at 3.39 microns or 0.63 microns can be detected with this method. No dye is used in this method as a absorption or reaction medium.

The use of dye in intracavity dye laser spectroscopy (IDLS) is known to give greater versatility over intracavity absorption since different dyes acting as absorbing media will give different modes in the spectra ("Intracavity Laser Tomography of $C_2$ in a Oxyacetylene Flame, Harris and Weiner, Opt. Lett., Vol.6, p.434 (1981); "Power Dependence of Continuous Wave Intracavity Spectroscopy", Harris, Opt. Lett. Vol. 7, P.497 (1982)). However, the modes must be matched with the absorber to be detected. The number of modes obtained per dye is limited, so use is restricted. The dye is not chemically reactive with the sample gas.

Wolber (U.S. Pat. No. 3,732,017) teaches analyzing an unknown gas with a tunable laser having a known gas in the laser cavity so that the laser will lase only at the frequencies of the known gas. The unknown gas is illuminated with the reference spectrum of the known gas. Some or all of the peaks will be absorbed if the unknown gas is partially or completely composed of gases identical to the known gas. The use of a chemically reactive dye is not taught.

Giuliani (U.S. Pat. No. 4,513,087) teaches detecting small amounts of chemicals such as ammonia, hydrazine and pyridine with a capillary tube having the outer surface coated with a dye film such as oxazine perchlorate, which, when exposed to these chemicals, changes color. The capillary tube serves as a multiple total reflective medium for an optical beam from a light emitting diode. When the color of the coating changes, the multiply-reflected light in the tube is modified and the presence of the chemical is indicated by the change in output light intensity from the capillary tube. The device is reusable since removing the chemical from the presence of the dye restores the original color. Sensitivity is down to less than 60 ppm. Response time is not instantaneous but takes one to two minutes for the vapor to permeate into the coating and an equal amount of time for the color change to reverse so the detector can be reused.

A system which can detect small concentrations of chemical vapors and gases, can respond instantaneously and can be regenerated for reuse as needed. Simple operation for field use would also be an advantage over prior art.

SUMMARY OF THE INVENTION

Accordingly, it is an object of this invention to use a free-flowing liquid lasing dye jet stream to detect chemical vapors instantaneously.

Also, it is an object of this invention to eliminate the need for a separate absorbing element to be placed in a lasing dye cavity to detect vapors in the atmosphere.

And, it is an object on this invention to have a device of simple operation for field use.

Furthermore, it is an object of this invention to improve the detection limit of chemical vapors to 1 part per billion.

Finally, it is an object of this invention to improve the time for regeneration of the dye reactant for reuse.

These and other objects are accomplished by a lasing dye sensor system and method that uses a free-flowing pumped lasing dye jet stream which, when exposed to an ambient air sample, undergoes a chemical reaction with vapors in the air sample, resulting in a change in optical properties of the lasing dye itself, such as shifting the lasing dye frequency or reducing its intensity.

BRIEF DESCRIPTION OF THE DRAWINGS

The invention may be better understood by reference to following drawings in which like numerals in different figures represent the same structures or elements.

DETAILED DESCRIPTION OF THE INVENTION

As described above, a lasing dye sensor system uses a lasing dye which emits a particular wavelength when activated by a laser beam. This wavelength is absorbed by a chemical vapor or gas of analytical interest. In the claimed invention, it is the lasing dye itself which is modified by direct contact with the chemical vapor or gas of analytical interest resulting in a shift in color or intensity.

One class of lasing dyes in which a color shift occurs are the oxazine dyes having the general structures below:

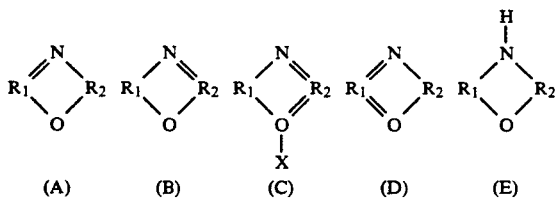

(A)  (B)  (C)  (D)  (E)

wherein $R_1$ is an aryl or aryl substituted with amino groups, amino groups substituted with alkyls, hydroxyl groups, oxyl groups, haloxyl groups, carboxyl groups, sulphoxyl groups or an combination thereof, $R_2$ is an aryl, diaryl or aryl/diaryl substituted with amino groups, amino groups substituted with alkyls, hydroxyl groups, oxyl groups, haloxyl groups, carboxyl groups, sulphoxyl groups or any combination thereof and X are halides or an oxyl group. The preferred oxazine compound is of structure (A) having $R_1$ as an aryl substituted with an amino group, an amino group substituted with a methyl or ethyl group, or a sulfoxyl group, $R_2$ as a diaryl substituted with an amino group, an amino group substituted with a methyl or ethyl group, an oxyl group, a hydroxyl group or an alkyl. The most preferred compound is oxazine perchlorate of the following structure:

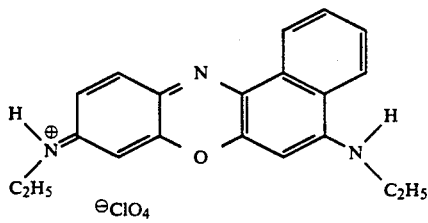

Figure 1A:
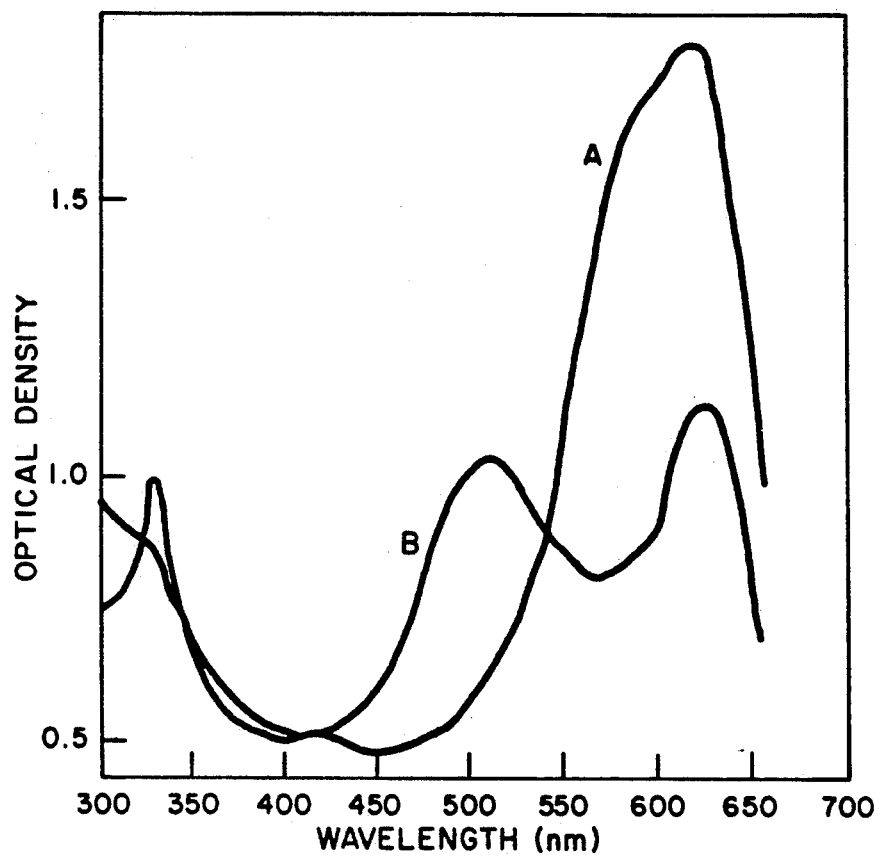
FIG. 1A shows the spectral changes of a $10^{-5}M$ solution of oxazine perchlorate in ethyl alcohol before (A) and after (B) the addition of a one percent concentration of ammonium hydroxide.
Figure 1B:
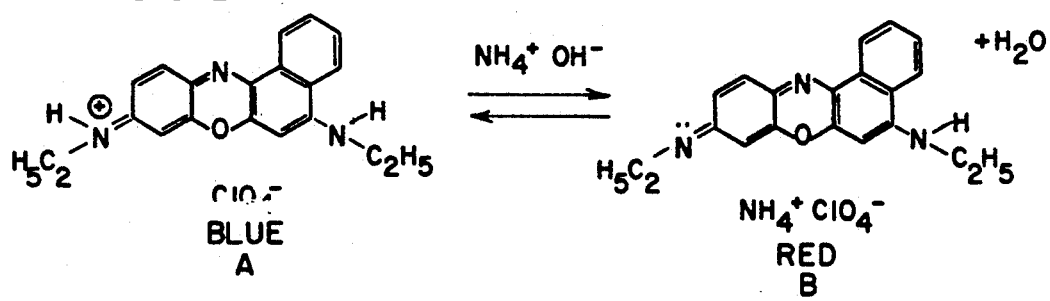
FIG. 1B is a diagram which shows the chemical change which oxazine perchlorate undergoes upon exposure to ammonia.

The electron withdrawing property of the central N-atom in this class of dyes causes the end groups in these dyes to be acidic. The addition of a small amount (in the part-per-billion range) of basic chemical vapor or gas of analytical interest will increase the pH and produce a color change due to the deprotonation on one of the amino (i.e. auxochrome) end groups. As shown in FIG. 1A, a $10^{-5}M$ solution of oxazine perchlorate in ethanol changes color from blue to red upon exposure to ammonia or hydrazine. The change in chemical structure is shown in FIG. 1B.

A lasing dye system is designed to have a jet stream of lasing dye flow into a chamber. In the claimed invention, modification to the chamber allows access of an air sample containing a chemical vapor or gas of analytical interest to come into contact with the lasing dye flow stream. The lasing dye in the chamber reacts with a particular chemical vapor or class of chemical vapors in the air sample such that the chemical reaction causes the lasing dye to change color. This color change, in turn, causes a detectable shift in the lasing wavelength and/or lasing intensity of the pumped lasing dye.

Figure 2:
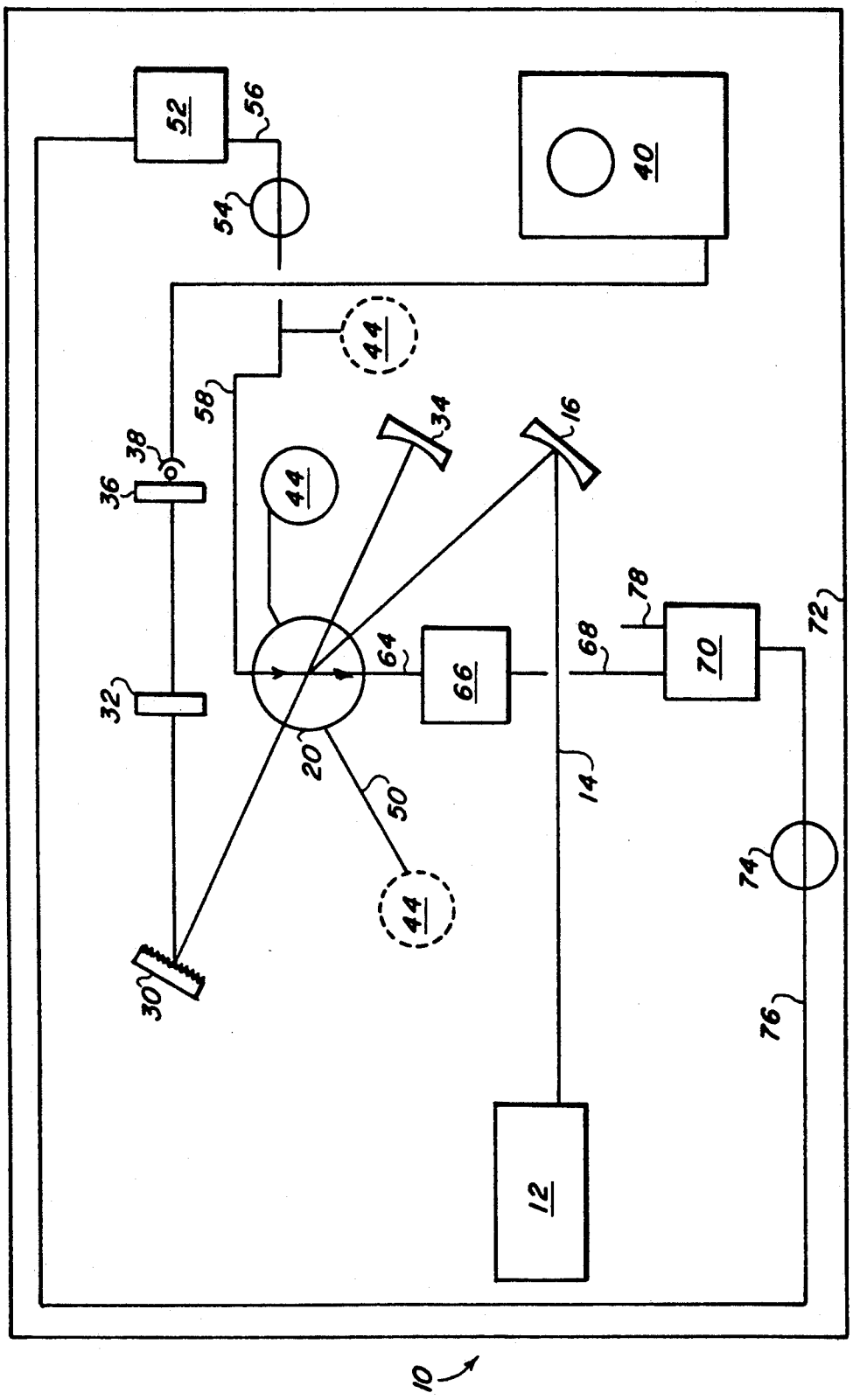
FIG. 2 is a schematic of the free-flowing lasing dye sensor system.
Figure 3:
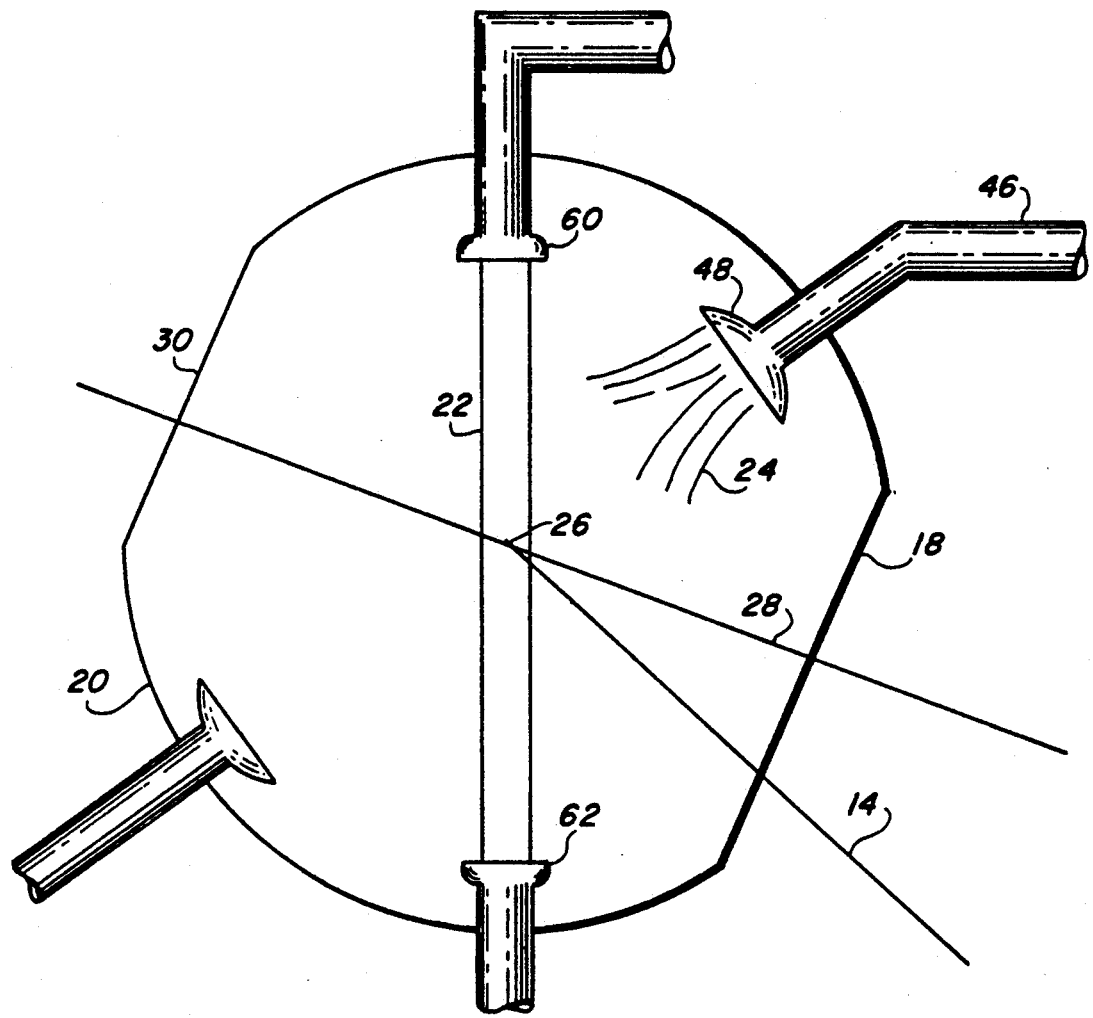
FIG. 3 is a schematic of the chamber within the free-flowing lasing dye sensor.

Referring now to the drawings wherein like reference numerals designate identical or corresponding parts throughout the several views, and more particularly to FIGS. 2 and 3 thereof, the lasing dye system 10 has a low power external pump laser 12 which produces a laser beam 14 that is reflected by the pump mirror 16 through an optical window 18 into a chamber 20 in which the laser beam 14 intersects with a jet stream of liquid dye 22 and a sample of air potentially containing contaminants as a chemical vapor or gas of analytical interest 24. The external pumping laser beam may be generated by any other known mean of producing a laser beam, such as a laser diode. At this intersection point 26 the pumped dye in the jet stream reacts with chemical vapors contained in the air sample. The free flowing dye lases and emits certain wavelengths 28 which then pass through an optical window 32 and on to a tunable grating 30. Reaction of the chemical vapors in the sample with the pumped lasing dye modifies the dye and changes the dye's emission spectra.

The tunable grating 32 selectively reflects the light to a beam splitter such as a half-silvered chamber output mirror 36 that partially reflects the light back to the grating 30 through the intersection point 26 of the jet stream of liquid dye, the laser beam and air sample. The light is then reflected back through the intersection point 26 by a chamber mirror 34. This cycle repeats until the spectral signal is strengthened enough to pass through the half-silvered chamber output mirror 34 to a filter 38 and then on to a photodetector 40. The photodetector 40 sends a signal to a scope monitor 42 which monitors the spectra of the pumped lasing dye.

The air sample is collected from the atmosphere by an air pump 44 or similar device such as a fan which transfers the air sample through a conduit 46 to a nozzle 48 where the air sample is injected into the chamber 20. An outlet 50 in the chamber 20 allows the air to exit back to the atmosphere. In the alternative, the pump 44 is connected to the outlet 50 and draws air sample into and through the chamber 20. The pump 44 can be operated continuously or intermittently as required.

The free-flowing lasing dye comes from a reservoir 52 of dye that is chemically-reactive with particular chemical vapors. The dye is transferred by a pump 54 through a conduit 56 from the reservoir 52 through another conduit 58 to the dye nozzle injector 60 within the chamber 20. In one embodiment of this invention, the air is injected by the pump 44 into the conduit 58 leading into the nozzle injector 60. The dye flows into open space in the chamber 20 where it interacts with the air sample 24 after which it flows to a dye collector 62 within the chamber 20. The dye collector 62 receives the dye stream which is transferred through a conduit 64 to a second reservoir 66.

The contaminated dye is transferred to a recycling system through a conduit 68 in which the dye is collected in a vessel 70. The chemical reaction is reversed by any known means for reversing chemical reactions, such as aerating, heating or adding another reactant to neutralize the reaction, and the dye is restored to its original lasing properties, including color and structure. The restored dye is pumped through a conduit 72 by a pump 74 and recirculated into the original dye reservoir 52 through a conduit 76. The chemical vapor is removed through a conduit 74 in the collection vessel 70. It can be returned to the atmosphere or, if toxic or otherwise harmful to the environment, it can be disposed of by any known means for treating toxic wastes.

The reaction time of the lasing dye system is instantaneous. Its sensitivity is as low as one part per billion. This invention is an improvement over solid detectors and discloses a new use for a free-flowing lasing dye jet stream system which eliminates the need for a separate absorbing element for analysis and detection and uses the lasing dye itself as the sensor for chemical vapors or gases.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States is:

1. An external lasing dye system for detecting a chemical vapors having a basic pH in an air sample having:
   (a) a chamber;
   (b) a means for generating and projecting a laser beam into the chamber;
   (c) a means for introducing a free-flowing jet stream of lasing dye into the chamber so that the lasing dye jet stream intersects the laser beam; and
   (d) a means for detecting and analyzing the lasing emission spectra of the lasing dye jet stream;
   wherein the improvement comprises:
   a) a means connected to the lasing dye system for conveying an air sample potentially containing contaminants having a basic pH into the chamber so that the air sample contacts a dye stream introduced into the chamber, said dye stream being chemically reactive with the contaminants, and the contact between the air sample and the dye stream occurring not later than the dye streams intersection with the laser beam, whereby chemical reaction between the dye stream and the contaminants change the spectra emitted by said lasing dye; and
   b) a collecting means in flow concentration with said chamber for recovering the lasing dye after intersection with the laser beam.

2. An apparatus as recited in claim 1 wherein a regenerating means in flow communication with said collecting means receives the lasing dye from the collecting means and removes any contaminants absorbed by the lasing dye from the air sample to make the dye reusable by restoring its original lasing properties.

3. An apparatus as recited in claim 2 wherein the means for generating a laser beam is a laser diode.

4. An apparatus as recited in claim 3 wherein the conveying means introduces the air sample to the free-flowing pumped lasing dye jet stream at the intersection of the laser beam and dye stream in the chamber.

5. An apparatus as recited in claim 3 wherein the conveying means introduces the air sample to the lasing dye jet stream prior to the intersection of the external pumping laser beam and lasing dye jet stream in the chamber.

6. An apparatus as recited in claim 4 wherein the conveying means sample comprises:
   a. an inlet in the chamber;
   b. a fan which moves air into the inlet and to the intersection of the free-flowing pumped lasing dye jet stream and the external pumping, laser beam; and
   c. an outlet which permits the air to exit the chamber to the atmosphere.

7. An apparatus as recited in claim 4 wherein the conveying means comprises:
   a. an inlet in the chamber open to the atmosphere;
   b. an outlet in the chamber; and
   c. a pump connected to the outlet which draws air into the chamber through the inlet and out of the chamber through the outlet so that the air contacts the dye at the intersection of the dye stream and the laser beam.

8. An apparatus as recited in claim 5 wherein the conveying means comprises:
   a. an inlet to a pipe carrying dye to the chamber;
   b. an air pump which forces air into the inlet and to the dye moving to the intersection of the dye stream and the laser beam.

9. An apparatus as recited in claim 2 wherein the contaminants are chosen from the group consisting from ammonia and hydrazine.

10. An apparatus as recited in claim 9 wherein the regenerating means is a vessel containing the dye which is aerated to evolve the ammonia or hydrazine absorbed by the dye and restore the dye to its original color and structure.

11. An apparatus as recited in claim 10 wherein the dye is an oxazine dye of the following general structures:

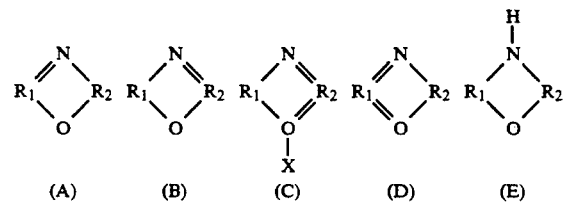

wherein $R_1$ is chosen from the group consisting of an aryl and an aryl substituted with amino groups, amino groups substituted with alkyls, hydroxyl groups, oxyl groups, haloxyl groups, carboxyl groups or sulphoxyl groups, $R_2$ is chosen from the group consisting of an aryl, diaryl and aryl or diaryl substituted with amino groups, amino groups substituted with alkyls, hydroxyl groups, oxyl groups, haloxyl groups, carboxyl groups or sulphoxyl groups and X is are chosen from the group consisting of halides and an oxyl group.

12. An apparatus as recited in claim 11 wherein the oxazine dye is structure (A) having $R_1$ as an aryl substituted with an amino group, an amino group substituted with a methyl or ethyl group, or a sulphoxyl group, $R_2$ as a diaryl substituted with an amino group, an amino group substituted with a methyl or ethyl group, an oxyl group, a hydroxyl group or an alkyl.

13. An apparatus as recited in claim 12 wherein the dye is oxazine perchlorate of the following structure:

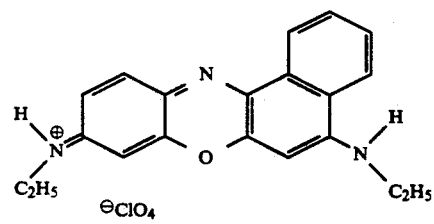

14. An apparatus as recited in claim 13 wherein the dye is a $10^{-5}$M solution of oxazine perchlorate in ethanol.

* * * * *